(12) United States Patent
Yazawa et al.

(10) Patent No.: US 7,714,885 B2
(45) Date of Patent: May 11, 2010

(54) ENDOSCOPE IMAGING APPARATUS

(75) Inventors: Nobuyoshi Yazawa, Hachioji (JP); Fuminori Tanahashi, Shirakawa (JP); Masami Shimizu, Hachioji (JP); Takao Yamaguchi, Hachioji (JP); Hiroyuki Kuroda, Hachioji (JP); Satoshi Takekoshi, Hachioji (JP)

(73) Assignee: Olympus Corporation, Tokyo (JP)

( * ) Notice: Subject to any disclaimer, the term of this patent is extended or adjusted under 35 U.S.C. 154(b) by 768 days.

(21) Appl. No.: 10/081,940

(22) Filed: Feb. 22, 2002

(65) Prior Publication Data

US 2003/0169333 A1    Sep. 11, 2003

(51) Int. Cl.
A62B 1/04    (2006.01)
A61B 1/04    (2006.01)

(52) U.S. Cl. .......................................... 348/65; 348/75
(58) Field of Classification Search .................... 348/42, 348/45, 51–53, 61, 65, 72, 75–77
See application file for complete search history.

(56) References Cited

U.S. PATENT DOCUMENTS

| | | | |
|---|---|---|---|
| 4,972,268 A | | 11/1990 | Frederick et al. |
| 5,090,259 A | * | 2/1992 | Shishido et al. ............ 73/866.5 |
| 5,413,107 A | * | 5/1995 | Oakley et al. ............... 600/463 |
| 5,520,222 A | * | 5/1996 | Chikama .................... 138/118 |
| 5,569,161 A | * | 10/1996 | Ebling et al. ................. 600/121 |
| 5,577,991 A | * | 11/1996 | Akui et al. ................... 600/111 |
| 5,776,049 A | * | 7/1998 | Takahashi .................... 600/111 |
| 5,876,326 A | * | 3/1999 | Takamura et al. ............ 600/110 |
| 6,110,106 A | * | 8/2000 | MacKinnon et al. ......... 600/181 |
| 6,117,071 A | * | 9/2000 | Ito et al. ....................... 600/168 |
| 6,485,409 B1 | * | 11/2002 | Voloshin et al. ............. 600/115 |
| 6,807,295 B1 | * | 10/2004 | Ono ............................ 382/154 |
| 6,826,424 B1 | * | 11/2004 | Zeng et al. ................... 600/476 |

FOREIGN PATENT DOCUMENTS

| | | |
|---|---|---|
| EP | 0 978 251 A1 | 2/2000 |
| JP | 61-19584 | 6/1986 |
| JP | 07-155291 | 6/1995 |
| JP | 08-248465 | 9/1996 |
| JP | 10-127568 | 5/1998 |
| JP | 2000-075218 | 3/2000 |
| JP | 2000-139817 | 5/2000 |
| JP | 2001-008886 | 1/2001 |

* cited by examiner

Primary Examiner—David Czekaj
(74) Attorney, Agent, or Firm—Scully, Scott, Murphy & Presser, P.C.

(57) ABSTRACT

An endoscope imaging apparatus includes an imaging unit in which an imaging optical unit that contains at least one optical lens in a rigid member the one end side of which is airtightly sealed is airtightly joined to an imaging element unit that contains at least one imaging element in a rigid member the one end side of which is airtightly sealed through a tubular member to which a bellows portion having an elastic force is formed.

26 Claims, 9 Drawing Sheets

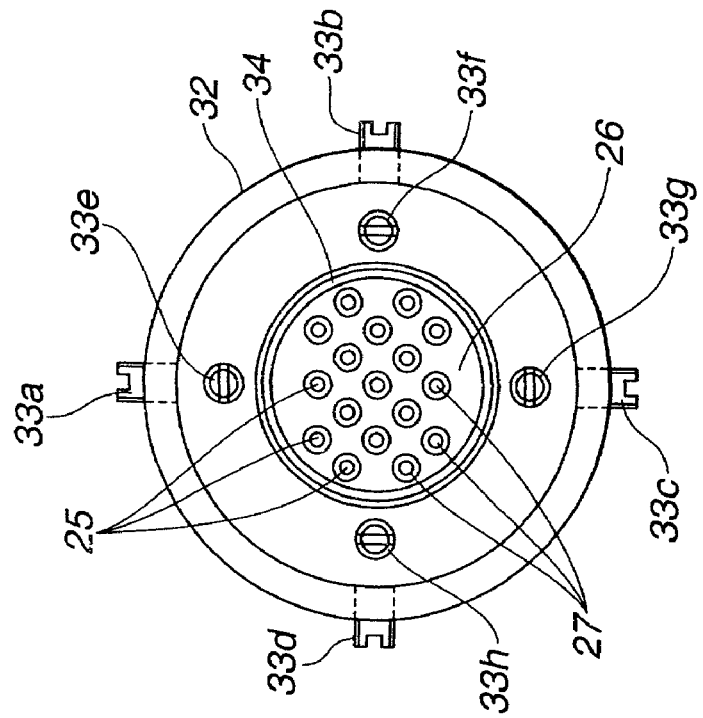
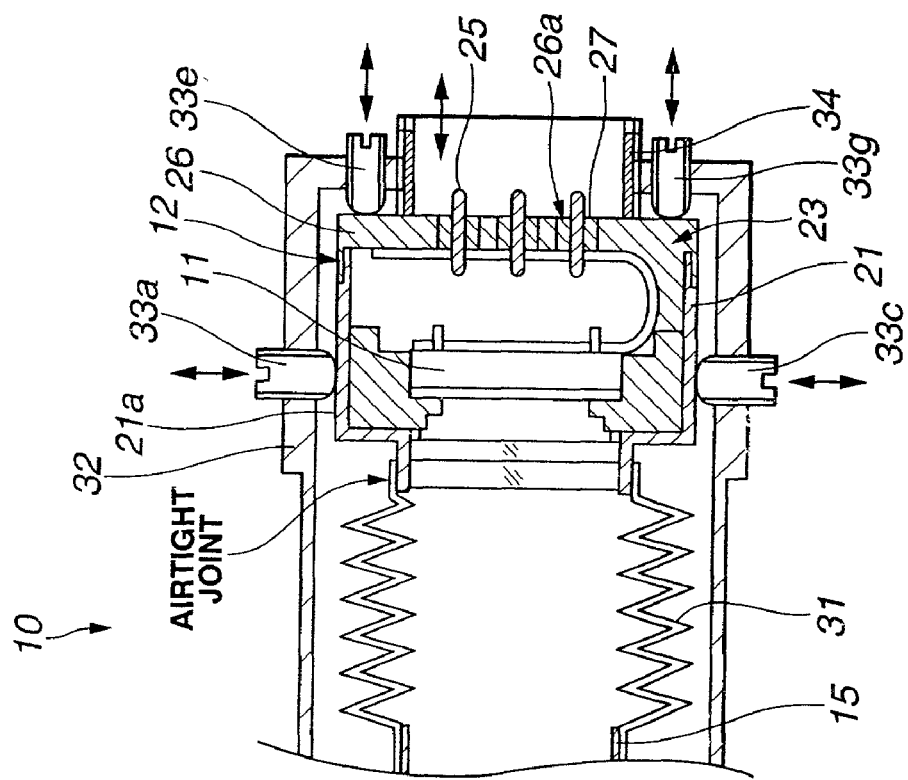

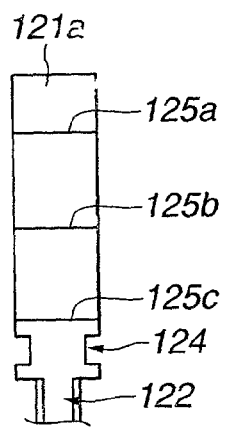
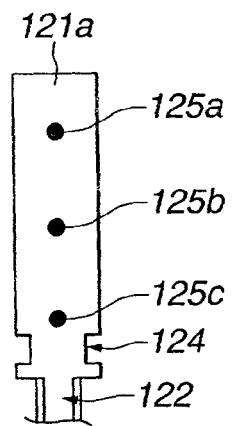
FIG.9A FIG.9B
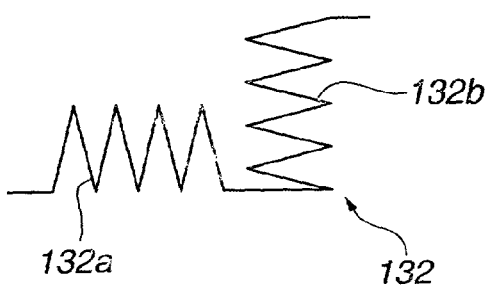
FIG.10
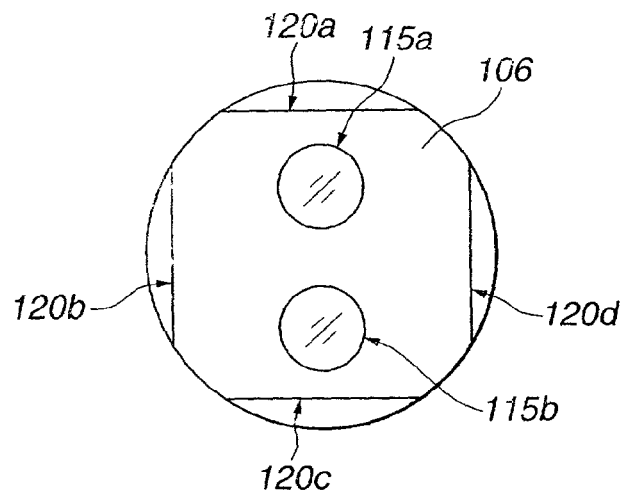
FIG.11

ENDOSCOPE IMAGING APPARATUS

This application claims benefit of Japanese Application No. 2000-333632 filed on Oct. 31, 2000, the contents of which are incorporated by this reference.

BACKGROUND OF THE INVENTION

1. Field of the Invention

The present invention relates to an endoscope imaging apparatus including an imaging unit having an imaging optical unit and an imaging element unit.

2. Description of Related Art

Conventionally, there are widely employed endoscope imaging apparatuses connected to an optical observation tube, and the like inserted into a body to display an endoscope image on a screen such as a monitor, and the like by converting an optical image captured by the optical observation tube into electric signals.

For example, Japanese Unexamined Patent Application Publication No. 8-248465, Japanese Examined Utility Model Publication No. 61-19584, U.S. Pat. No. 4,972,268, and the like disclose ideas as to the adjustment of the position where an imaging element is disposed with respect to an imaging optical system and as to the attachment structure of the imaging element.

Recently, endoscope imaging apparatuses, and the like having a possibility that they are indirectly in contact with organs, and the like when they are in use must be sterilized and disinfected after it has been used. Autoclave sterilization is available as the sterilization means. The autoclave sterilization is high temperature high pressure steam sterilization, operates at low running cost, and has high reliability.

In the autoclave sterilization, however, since endoscope imaging apparatuses are exposed to high temperature and high pressure steam, the entry of the steam into the inside of the imaging apparatuses must be prevented. To cope with this problem, the endoscope imaging apparatus is required to have water tightness, which prevents the entry of a liquid in the inside of the apparatus even if it is dipped in the liquid, and air tightness that is more higher than that in an ordinary atmospheric pressure.

Accordingly, metal, ceramics, glass, and a crystalline material that prevent the permeation of high temperature and high pressure, and a resin material, and the like that have very small stream permeability are selectively used as a material for constituting the endoscope imaging apparatus. In contrast, an air tight joint, for example, soldering, brazing, and the like is used as a joint means for joining materials with each other, in which metal, ceramics, glass, a crystalline material, and the like are used as a main component of the joint.

For example, Japanese Unexamined Patent Application Publication No. 2000-075218 discloses an endoscope apparatus in which an outer sheath is composed of metal as far as possible and a joint is airtightly joined by soldering. In this endoscope apparatus, a space in an optical axial direction, in which an optical system moves, is covered making use of a metal bellows.

However, in the many ideas described above as to the position adjustment and the attachment structure of the imaging element, adjustment in optical axis direction, adjustment of decentering, adjustment of tilt, and the like are carried out independently. Since the imaging element is arranged to cope with all the adjustments, when all the adjustments are combined, the number of parts of the endoscope imaging apparatus is greatly increased, from which a problem arises in that cost is increased, the size of the apparatus is increased, and the adjustment of the apparatus is troublesome.

It is contemplated to arrange all the components from an imaging optical system to an imaging element in an airtight sealed state for preventing the entry of steam from the outside. In this arrangement, however, it is difficult to perform the aforementioned positional adjustment of the imaging optical system and the imaging element and to provide the aforementioned attachment structure with them. Further, the provision of the above structure results in such disadvantages that the size of the apparatus is further more increased and that various adjustments must be performed before the components are airtightly sealed as well as an allowable level to an optical performance is reduced by performing the various adjustments before they are airtightly sealed.

Further, recently, a technology for performing diagnosis using special light such as infrared light, fluorescent light, and the like is becoming widespread. For example, Japanese Unexamined Patent Application Publication No. 7-155291 discloses a fluorescent light observation endoscope apparatus having a rotary filter disposed therein, rotated by a motor, and including a filter formed of an optical lens for passing white light therethrough and a similar filter for passing fluorescent light of a particular band therethrough. This endoscope imaging apparatus can also perform observation with fluorescent light by disposing a filter corresponding to the fluorescent light by rotating the rotary filter according to a type of illumination light emitted from a light source.

In addition to the above apparatuses, there is also an endoscope imaging apparatus arranged separately from an optical adaptor acting as a lens unit so that it can perform observation with special light through a dedicated optical adaptor to which a filter for observation with special light is attached.

To permit the aforementioned fluorescent light observation endoscope apparatus to be subjected to autoclave sterilization, however, it is necessary to dispose the rotary filter and the motor in an airtight unit. Then, there is a possibility not only that a structure in which they are disposed is made complex and expensive but also that the apparatus is increased in size and weight and imposes a burden on a user and that the operability of the apparatus is lowered.

Further, when the endoscope imaging apparatus is arranged separately from the optical adaptor, they must be autoclave-sterilized individually. Accordingly, the endoscope imaging apparatus must be connected to the optical adaptor in a state in which the joint thereof is sufficiently dried after the apparatus is autoclave-sterilized. This is because that when the joint is dried insufficiently, there is a possibility that a cover glass in the vicinity of the joint tarnishes while the apparatus is being used. That is, in this separate arrangement, there is a possibility that the advantage of the autoclave sterilization that the apparatus can be used at once after it is sterilized can not be exhibited.

Further, there are conventionally proposed endoscopes the operability of which is improved by removing angle down by disposing a small motor at an extreme end. For example, Japanese Unexamined Patent Application Publication No. 10-127568 proposes a zoom type endoscope capable of performing a stable zoom drive even if a small motor having a small output is used. Further, Japanese Unexamined Patent Application Publication No. 2001-008886 proposes an endoscope having an air vent disposed at a part of a moving lens frame so that a moving lens can move smoothly.

However, in the zoom type endoscope of Japanese Unexamined Patent Application Publication No. 10-127568, since an optical member moving mechanism, which acts as a target lens moving frame and lens frame support member, is directly mounted on a rotary power source, it is necessary to assemble them with a pinpoint accuracy, and thus a structure is increased in size and made complex.

In contrast, in the endoscope disclosed in Japanese Unexamined Patent Application Publication No. 2001-008886, since an optical member moving mechanism is disposed spaced apart from a power source, a drive force is transmitted by a push/pull operation in place of the transmission thereof by rotation.

A first object of the present invention is to provide an endoscope imaging apparatus in which an imaging optical system and an imaging element are airtightly sealed and in which the positions of the imaging optical system and the imaging element can be easily adjusted from the outside of these components having been airtightly sealed.

A second object of the present invention is to provide an endoscope imaging apparatus which can airtightly seal an imaging optical system and an imaging element, improve an optical capability, and reduce the size thereof at a less expensive cost.

A third object of the present invention is to provide an endoscope imaging apparatus which can easily change filters, is excellent in operability, has a simple structure, is less expensive, and can be subjected to autoclave sterilization.

A fourth object of the present invention is to provide an endoscope imaging apparatus that transmits rotation from a rotary power source for moving optical members such as a lens, and the like, and makes complex axial alignment of pinpoint accuracy unnecessary.

SUMMARY OF THE INVENTION

In an endoscope imaging apparatus of the present invention, the endoscope imaging apparatus includes an imaging unit in which an imaging optical unit that contains at least one optical lens in a rigid member one end side of which is airtightly sealed is airtightly joined to an imaging element unit that contains at least one imaging element in a rigid member one end side of which is airtightly sealed integrally with each other through a tubular member to which a bellows portion having an elastic force is formed. The imaging optical unit and the imaging element unit airtightly joined to each other through the tubular member can change a distance or a relative inclination.

The above and other objects, features and advantages of the invention will become more clearly understood from the following description referring to the accompanying drawings.

BRIEF DESCRIPTION OF THE DRAWINGS

FIGS. 1 to 3 show a first embodiment of the present invention.

FIG. 1 is a view showing an endoscope system to which an endoscope imaging apparatus is applied.

FIG. 2 is a view explaining an imaging unit of an endoscope imaging apparatus arranged airtightly using a bellows member.

FIG. 3A is a lengthwise sectional view explaining an arrangement of the imaging unit in the vicinity of an imaging element unit.

FIG. 3B is a view of the imaging unit when it is viewed from a hermetic connector side.

FIGS. 7 to 12 show a fourth embodiment of the present invention.

FIG. 7 is a view explaining an arrangement of an endoscope imaging apparatus in its longitudinal section.

FIG. 8 is a view explaining the arrangement of the endoscope imaging apparatus in its vertical section.

FIG. 9A is a view explaining an example of marks disposed on an adjustment pin.

FIG. 9B is a view explaining another marks disposed on the adjustment pin.

FIG. 10 is a view explaining an arrangement of a bellows portion.

FIG. 11 is a view explaining another example of arrangement of a filter unit.

FIG. 12 is a view explaining another example of arrangement of the filter unit.

DETAILED DESCRIPTION OF PREFERRED EMBODIMENTS

A first embodiment of the present invention will be described with reference to FIGS. 1 to 3.

Figure 1:
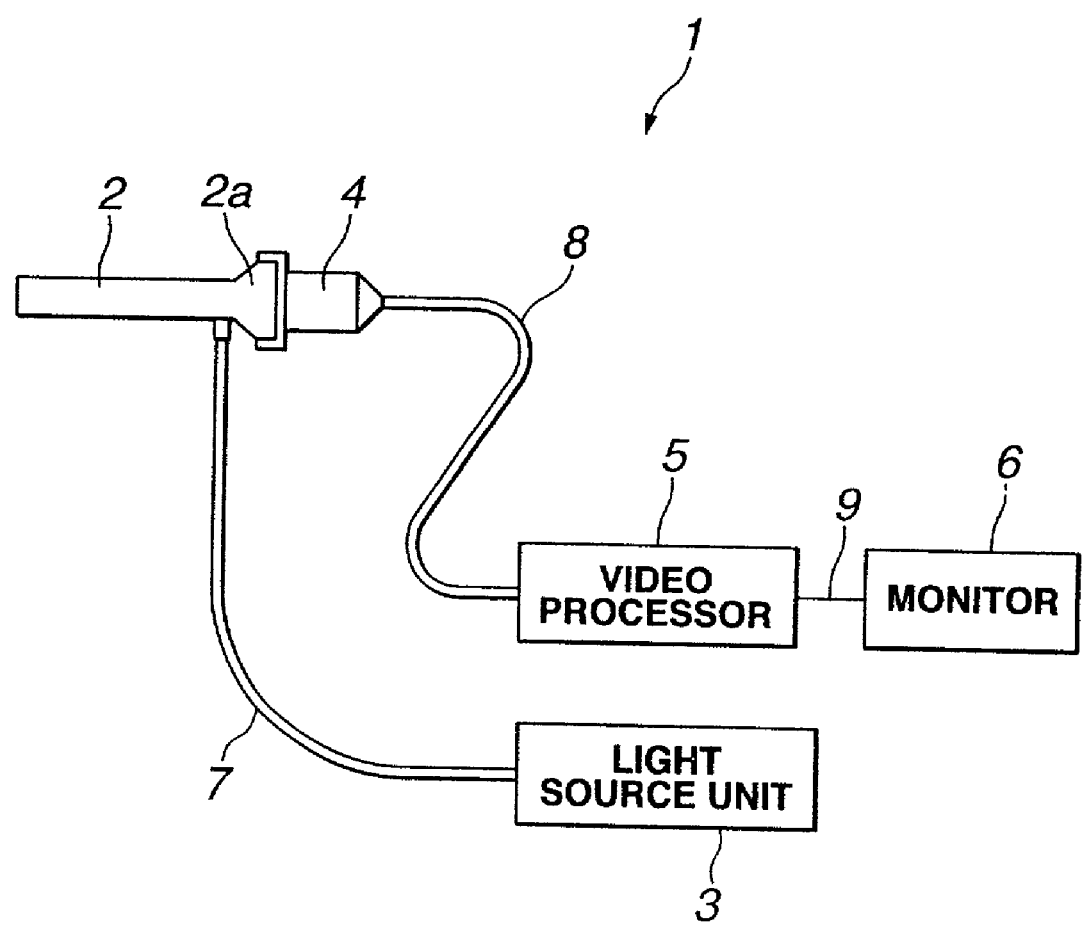

As shown in FIG. 1, an endoscope system 1 is mainly composed of an endoscope 2, a light source unit 3, an endoscope imaging apparatus 4, a video processor 5, and a monitor 6.

The endoscope 2 is used to observe, for example, the interior of a body cavity. The light source unit 3 supplies illumination light to the endoscope 2. The endoscope imaging apparatus 4 contains a solid imaging element, for example, a CCD or the like which will be described later. Then, the endoscope imaging apparatus 4 is connected to an eye contact portion 2a of the endoscope 2.

The video processor 5 is arranged as medical electric equipment. Then, the video processor 5 creates video signals from electric signals photoelectrically converted by the solid imaging element. The monitor 6 displays the video signals as an endoscope image.

Reference numeral 7 denotes a light guide cable for detachably connecting the endoscope 2 to the light source unit 3. Reference numeral 8 denotes a camera cable for detachably connecting the endoscope imaging apparatus 4 to the video processor 5. Reference numeral 9 denotes a video cable for detachably connecting the video processor 5 to the monitor 6.

Figure 2:
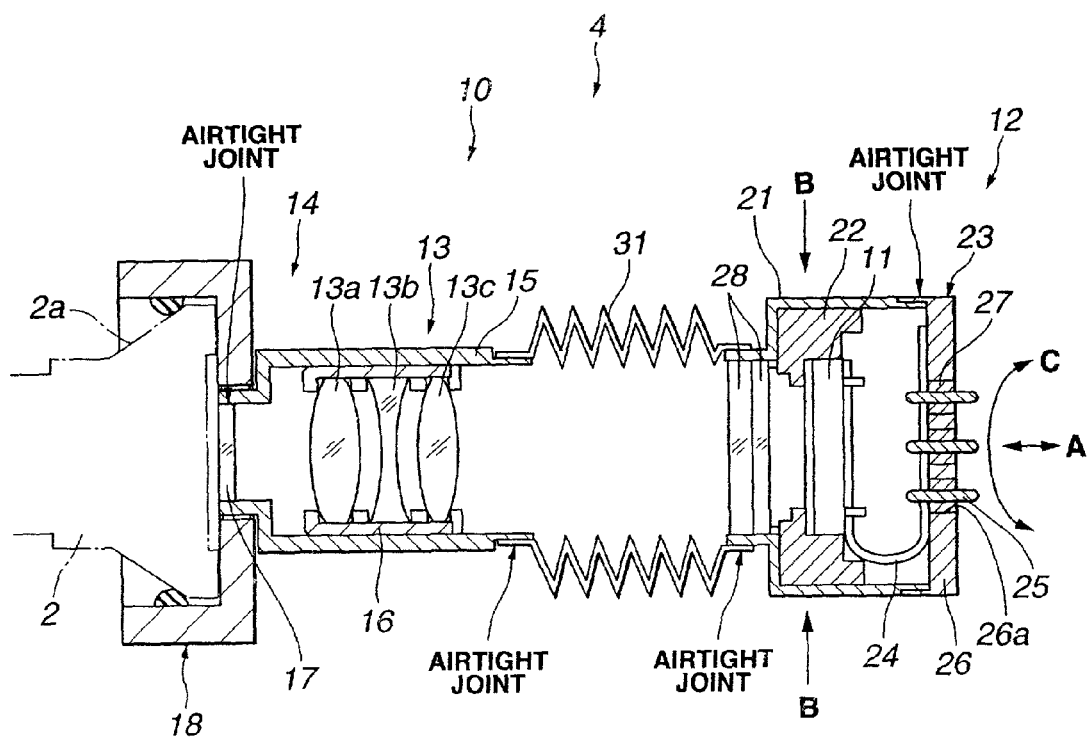

As shown in FIG. 2, an imaging unit 10 acting as a main component constituting the endoscope imaging apparatus 4 includes an imaging element unit 12 containing a CCD 11 and an imaging optical unit 14 containing an imaging optical system 13.

The CCD 11 records an endoscope image from the endoscope 2. The imaging optical system 13 forms the endoscope image on the imaging surface of the CCD 11 and is composed of, for example, a plurality of optical lenses 13a, 13b, . . . disposed therein.

The imaging optical unit 14 includes a metal imaging optical frame 15 composed of a stainless tubular material, or the like. A lens frame 16, in which the plurality of optical lenses 13a, 13b, . . . constituting the imaging optical system 13 are disposed, is fixed in the metal imaging optical frame 15 at approximately the center thereof.

A cover glass 17 is joined and disposed to the endoscope side, that is, the extreme end side of the imaging optical frame 15 in an airtight state by soldering, or the like, and the base end side, that is, the other end side of the imaging optical frame 15 is in an open state. An endoscope connection mechanical unit 18, which is detachably coupled with and fixed to the eye contact portion 2a of the endoscope 2, is disposed to the imaging optical unit 14 on the incident light side thereof.

In contrast, the imaging optical unit 12 includes a metal imaging element frame 21 composed of a stainless tubular material, or the like. A CCD receiver 22, to which the CCD 11 is fixedly disposed, is fixed to the imaging element frame 21 at approximately the center thereof.

A hermetic connector 23 is joined and disposed to the base end side of the imaging element frame 21 in an airtight state by soldering, laser welding, or the like. An end of a flexible substrate 24 is electrically connected to the CCD 11. An end of a contact pin 25 disposed to the hermetic connector 23 is electrically connected to the other end of the flexible substrate 24.

The hermetic connector 23 is composed of a metal frame 26, the contact pin 25 disposed in a through hole 26a formed through the metal frame 26 and connected to the other end of the flexible substrate 24, and an insulation member 27 of ceramics or the like for blocking the through hole 26a, in which the contact pin 25 is disposed, in an airtight state.

Various filters 28 such as a crystal filter, an IR cut filter, and the like are disposed on the extreme end side, which is the incident light side of the CCD 11, of the imaging element frame 21. Note that the signal line of the camera cable 8 is electrically connected to the other end of the contact pin 25 of the hermetic connector 23.

The imaging optical unit 14 is coupled with and fixed to the imaging element unit 12 through a tube member 31 acting as a tubular material having a deformable bellows portion formed thereto. The tube member 31, to which the bellows portion is formed, has corrosion resistance against steam as well as is formed of, for example, a thin stainless steel material, or the like, which is a material that does not pass a gas therethrough and provides an elastic force acting as a predetermined press force with the bellows portion.

The imaging optical unit 14, the imaging element unit 12, and the tube member 31 are specifically joined to each other airtightly by solder welding, laser welding, or the like, respectively in a state in which the respective ends of the tube member 31 are disposed around the outer peripheral surface of the opening of the imaging optical unit 14 and around the outer peripheral surface of the imaging element unit 12 on the incident light side thereof.

Since the imaging optical unit 14 is coupled with the imaging element unit 12 through the tube member 31 provided with the bellows portion that deforms in all directions as described above, it is possible to change the positional relationship between the imaging optical unit 14 and the imaging element unit 12 in a state in which the endoscope connecting mechanical unit 18 integrated with the imaging optical unit 14 is connected and fixed to the eye contact portion 2a of the endoscope 2.

That is, the focus of an endoscope image can be adjusted by moving the imaging element unit 12 back and forth in an optical axis direction that is the direction of an arrow A with respect to the imaging optical unit 14. Further, an adjustment for aligning the center of an endoscope image with the center of the imaging surface of the CCD 11 can be performed by moving the imaging element unit 12 in a direction perpendicular to an optical axis that is the direction of an arrow B with respect to the imaging optical unit 14.

Note that while only the two directions are shown by the arrows in the above description, the adjustment may be performed in two horizontal directions, in addition to the two vertical directions. Further, one-sided unsharpness of an endoscope image on the CCD can be adjusted by moving the imaging element unit 12 in a tilt direction to the optical axis, which is the direction of an arrow C, with respect to the imaging optical unit 14. The adjustment in the tilt direction may be performed also in a horizontal direction, in addition to a vertical direction.

An arrangement and operation of a specific adjustment mechanism of the imaging unit 10 arranged as described above will be described with reference to FIGS. 3A and 3B.

As shown in both the figures, a rigid adjustment frame 32, which is fixed to the imaging optical frame 15 integrally therewith by a not shown fixing method, is disposed to the outside of the imaging element unit 12.

A plurality of adjustment screws 33, the extreme end surfaces of which are abutted against the outside surface 21a of the imaging element frame 21, and an axial direction adjustment spacer 34, which has a male screw formed on the outer peripheral surface thereof abutting against the outside surface 26a of the hermetic connector 23, are screwed into and disposed to the adjustment frame 32 at predetermined positions, respectively.

The adjustment screws 33 include orthogonal direction adjustment screws 33a, 33b, 33c, and 33d, which are abutted against the outside surface 21a of the imaging element frame 21 and move the imaging element frame 21 in a direction orthogonal to the optical axis, and axial direction adjustment screws 33e, 33f, 33g, and 33h, which are abutted against the outside surface 26a of the hermetic connector 23 and move the imaging element frame 21 in the optical axis direction.

Note that the extreme ends of these adjustment screws 33a, . . . , 33h are formed in, for example, an approximately hemispherical shape, and the extreme ends thereof are in point contact with the respective outside surfaces. Further, a method of fixing the adjustment frame 32 to the imaging optical frame 15 includes, for example, a method of directly fixing the adjustment frame 32 to the imaging optical frame 15 and a method of interposing another member between the adjustment frame 32 and the imaging optical frame 15.

First, an adjustment of the imaging element unit 12 in the optical axis direction will be described here.

When the imaging element unit 12 is adjusted in the optical axis direction, the axial direction adjustment spacer 34, which is screwed into and disposed to the base end of the adjustment frame 32 so as to be abutted against the outside surface 26a of the hermetic connector 23, is rotated and moved back and forth in the axial direction.

That is, the bellows portion of the tube member 31 is contracted by rotating the axial direction adjustment spacer 34 in a predetermined direction and moving it forward, thereby the imaging element unit 12 is moved in the optical axis direction so as to approach the imaging optical unit 14.

In contrast, when the axial direction adjustment spacer 34 is rotated and moved back, the hermetic connector 23 is moved in a state in which it is abutted against the axial direction adjustment spacer 34 by the elastic force of the bellows portion of the tube member 31. That is, the imaging element unit 12 is moved in the optical axis direction so as to be spaced apart from the imaging optical unit 14.

As described above, the fine adjustment of the imaging element unit 12 in the optical axis direction with respect to the imaging optical unit 14 can be performed by changing the state in which the axial direction adjustment spacer 34 is screwed.

Next, an adjustment of decentering of the imaging element unit 12 will be described.

The decentering of the imaging element unit 12 is adjusted by rotating the orthogonal direction adjustment screws 33 screwed into and disposed to the adjustment frame 32 so as to be abutted against the outside surface 21*a* of the imaging element frame 21 so that the state in which the screws 33 are screwed is changed.

That is, the states in which the four orthogonal direction adjustment screws 33*a*, 33*b*, 33*c*, and 33*d* are screwed are adjusted, respectively according to a decentering state. With this operation, the center of an endoscope image having passed through the imaging optical unit 14 is aligned with the center of the effective imaging portion of the imaging surface of the CCD 11. Finally, the imaging element unit 12 is put into a fixed state by tightening the four orthogonal direction adjustment screws 33*a*, 33*b*, 33*c*, and 33*d* by a predetermined amount of force.

As described above, the decentering of the imaging element unit 12 with respect to the imaging optical unit 14 can be fine adjusted by changing the state in which the orthogonal direction adjustment screws 33*a*, 33*b*, 33*c*, and 33*d* are screwed.

Note that while it is described that the four pieces of orthogonal direction adjustment screws are used, three pieces of orthogonal direction adjustment screws may be used for the adjustment.

Finally, an adjustment of tilt of the imaging element unit 12 will be described.

The tilt of the imaging element unit 12 is adjusted by rotating the axial direction adjustment screws 33 screwed into and disposed to the adjustment frame 32 so as to be abutted against the outside surface 26*a* of the hermetic connector 23 so that the state in which the screws 33 are screwed is changed.

That is, a tilt state can be fine adjusted with respect to the optical axis of the imaging surface of the CCD 11 disposed to the imaging element unit 12 by adjusting the states in which the four axial direction adjustment screws 33*e*, 33*f*, 33*g*, and 33*h* are screwed, respectively according to the tilt state.

Note that the tube member to which the bellows portion is disposed is deformed in respective directions while maintaining elasticity with respect to the aforementioned three adjustments. Accordingly, these adjustments can be performed without applying a load on the airtight joint between the imaging optical unit and the imaging element unit.

As described above, the imaging optical unit is airtightly coupled with the imaging element unit through the metal tube member to which the bellows portion is disposed, whereas the adjustment screws and the spacer are disposed to the adjustment frame, which is disposed to the imaging optical unit integrally therewith, in the states in which they are screwed into the adjustment frame, whereby the imaging unit capable of performing the various adjustments of the axial direction, decentering, tilt, and the like. As a result, there can be provided the endoscope imaging apparatus the cost and size of which are decreased by the reduction of the number of parts and the man-hours for assembly and adjustment.

Further, since the various adjustments can be performed from the outside of the airtightly sealed unit, there can be provided the endoscope imaging apparatus the final optical performance of which is adjusted to an optimum state and which can cope with an airtight arrangement.

Note that, the fine adjustment of the imaging element unit 12 in the optical axis direction with respect to the imaging optical unit 14 may be performed by adjusting the states in which the four axial direction adjustment screws 33*e*, 33*f*, 33*g*, and 33*h* are screwed at the same time in the same direction.

With this operation, the arrangement of the apparatus can be simplified by omitting the axial direction adjustment spacer 34 from the base end of the adjustment frame 32.

Figure 4:
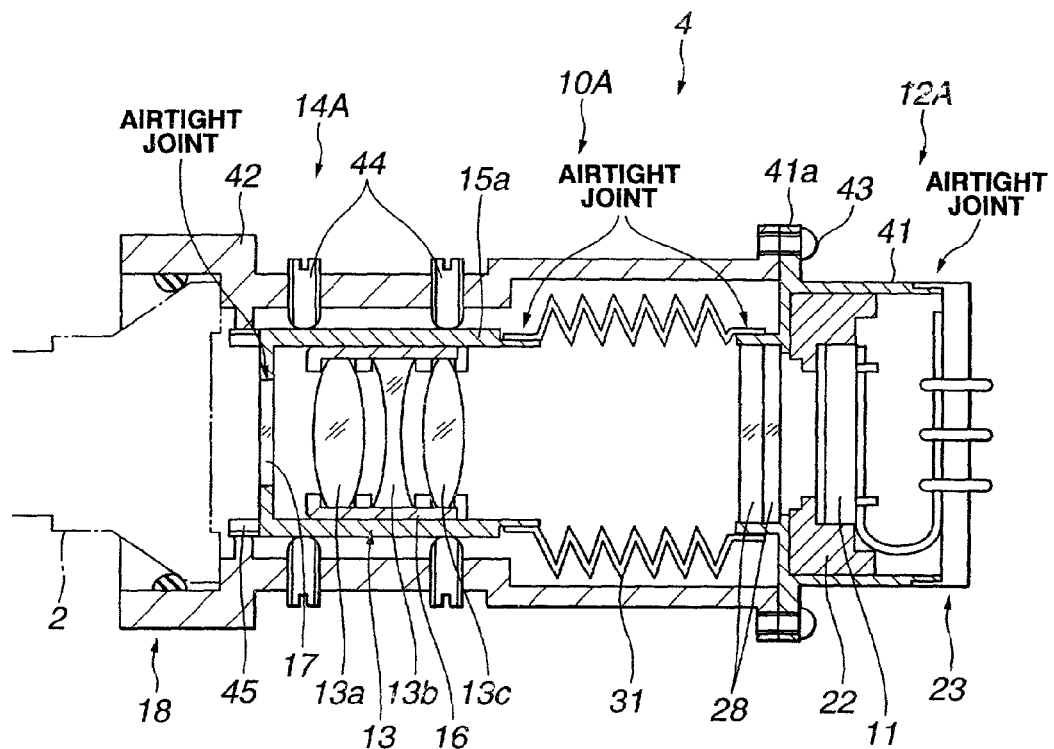
FIG. 4 is a view explaining other arrangement and operation of an adjustment mechanism of an endoscope imaging apparatus according to a second embodiment of the present invention.

FIG. 4 is a view explaining a second embodiment of the present invention.

This embodiment is arranged such that an imaging optical unit is adjusted in the state that an imaging element unit side is fixed, while, in the first embodiment, the various adjustments are performed by moving the imaging element unit in the state that the imaging optical unit is fixed.

As shown in the figure, in this embodiment, a flange portion 41*a* disposed to an imaging element frame 41, which constitutes an imaging element unit 12A, is integrally fixed, by fixing screws 43, to an adjustment frame 42 with which an endoscope connecting mechanical unit 18 is integrated.

In contrast, an imaging optical unit 14A is maintained in a predetermined state by that the extreme end surfaces of eight adjustment screws 44, which are screwed into and disposed to the adjustment frame 42, are abutted against an imaging optical frame 15*a*. Screws 44 are disposed in an axial direction at two positions at predetermined intervals. Then, screws 44 are disposed in the peripheral direction of a cross section vertical to an optical direction at four positions at predetermined angular angles. Further, the imaging optical unit 14A is disposed in a state in which the extreme end surface thereof is abutted against the base end surface of an axial direction adjustment spacer 45 screwed into and disposed to the adjustment frame 42 by the elastic force of the bellows portion of the above tube member 31.

Operation of an imaging unit 10A arranged as described above will be described.

First, when the imaging optical unit 14A is adjusted in an optical axis direction, the axial direction adjustment spacer 45 is rotated. With this operation, the imaging optical unit 14A can be fine adjusted by being moved back and forth in the optical axis direction with respect to the imaging element unit 12A.

Next, the decentering and tilt of the imaging optical unit 14A can be adjusted by appropriately rotating the eight adjustment screws 44 disposed to the adjustment frame 42.

As described above, the imaging optical unit is airtightly joined to the imaging element unit through the metal tube member to which the bellows portion is disposed, whereas the adjustment screws and the spacer are disposed to the adjustment frame integrated with the imaging element unit in the states in which they are screwed into the adjustment frame, thereby the various adjustments of the axial direction, decentering, tilt, and the like can be performed, similarly to the first embodiment. The other operations and advantages of the second embodiment are similar to those of the first embodiment.

Figure 5:
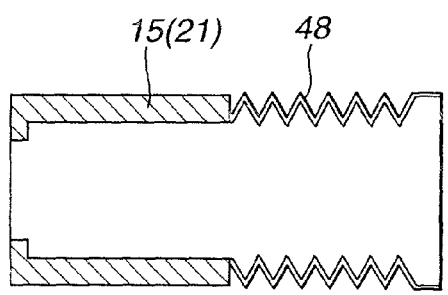
FIG. 5 is a view showing an example of arrangement of a frame member molded integrally with a bellows portion.

Note that the first and second embodiments described above show the examples of arrangement in which the tube member 31 to which the bellows portion is disposed is airtightly joined to the imaging optical frames 15 and 15a and to the imaging element frames 21 and 41, respectively. However, such an arrangement may be employed that a bellows portion is molded integrally with a frame member by, for example, electrodeposition thin film molding a bellows portion 48 to the imaging optical frame 15, as shown in FIG. 5. With this arrangement, workability in assembly can be improved by reducing the number of airtight joints from two joints to one joint.

Further, the frame member molded integrally with the bellows portion is not limited to the imaging element frame but may be disposed to the imaging element frame side.

Figure 6:
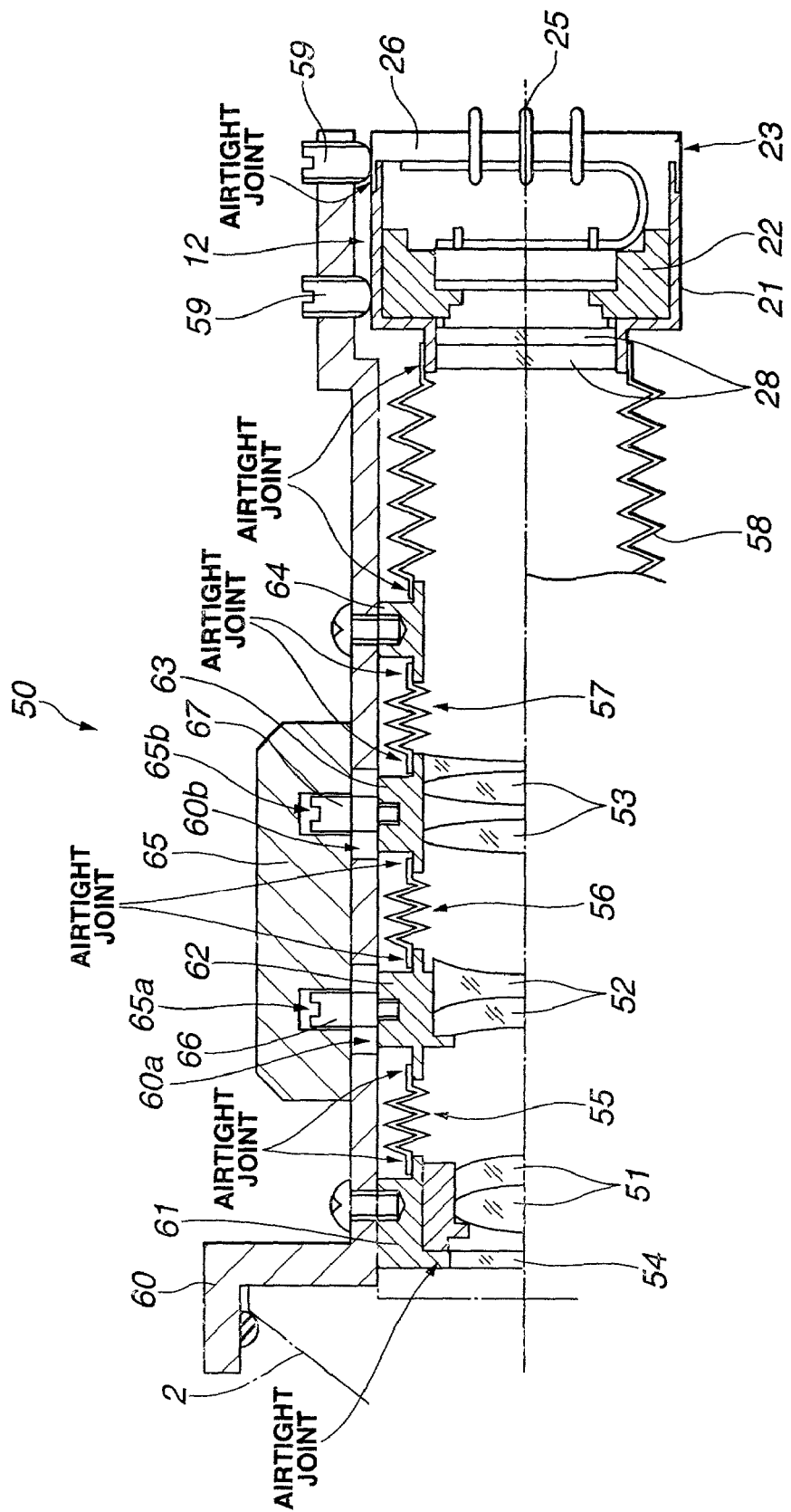
FIG. 6 is a view explaining other arrangement and operation of an adjustment mechanism of an endoscope imaging apparatus according to a third embodiment of the present invention.

A third embodiment of the present invention will be described below with reference to FIG. 6.

An imaging unit 50 arranged airtightly of this embodiment includes a variable power (zoom) optical system.

As shown in the figure, the imaging unit 50 of this embodiment is mainly composed of a first lens group frame 61 fixed to a main body frame 60 by, for example, screws, a second group lens frame 62 and a third lens group frame 63 that constitute a zoom optical system moving with respect to the main body frame 60, a fixed frame 64 fixed to the main body frame 60 by screws similarly to the first lens group frame 61, an imaging element unit 12 having the same arrangement as that of the first embodiment, tube members 55, 56, 57, and 58 each having a bellows portion for airtightly joining the lens frames, and a zoom ring 65 disposed on the outer periphery side of the main body frame 60.

The first group lens frame 61 contains first group lenses 51 and has a cover glass 54 airtightly joined to the incident light side thereof. The second group lens frame 62 contains second group lenses 52, and the third group lens frame 63 contains third group lenses 53.

Since the lens frames are airtightly joined by the tube members 55, 56, 57, and 58, respectively, the inner space from the first group lens frame 61 to which the cover glass 54 is airtightly joined to the imaging element unit 12 forms an airtight space that prevents the entry of steam from the outside.

Then, the imaging element unit 12 is held by eight adjustment screws 59 that are screwed into and disposed to the outer peripheral surface of the base end of the main body frame 60, similarly to the screws 44 of the second embodiment, in the state in which it can perform various positional adjustments.

Cam pins 66 and 67 project from the outer peripheral surfaces of the second and third group lens frames 62 and 63, respectively. These cam pins 66 and 67 project from long grooves 60a and 60b formed slenderly at predetermined positions of the main body frame 60 in an optical axis direction and are inserted into and disposed to cam grooves 65a and 65b that are formed around the inner peripheral surface of the zoom ring 65 obliquely with respect to an optical axis.

Accordingly, the rotation of the zoom ring 65 causes the cam pins 66 and 67 to appropriately move back and forth in the long grooves 60a and 60b in the optical axis direction, thereby wide angle observation or enlarged observation can be performed. The other arrangements of the third embodiment are the same as those of the aforementioned embodiments. Thus, the same components are denoted by the same reference numerals, and description thereof is omitted.

As described above, an endoscope imaging apparatus having the simple and less expensive arrangement and the variable power optical system can be made airtight by arranging the imaging unit by airtightly joining the frames through the tube members having the bellows portions. The other operations and advantages of the third embodiment are similar to those of the aforementioned embodiments.

A fourth embodiment of the present invention will be described below with reference to FIGS. 7 to 12.

An endoscope imaging apparatus of this embodiment can be subjected to autoclave sterilization and can change filters easily.

Figure 7:
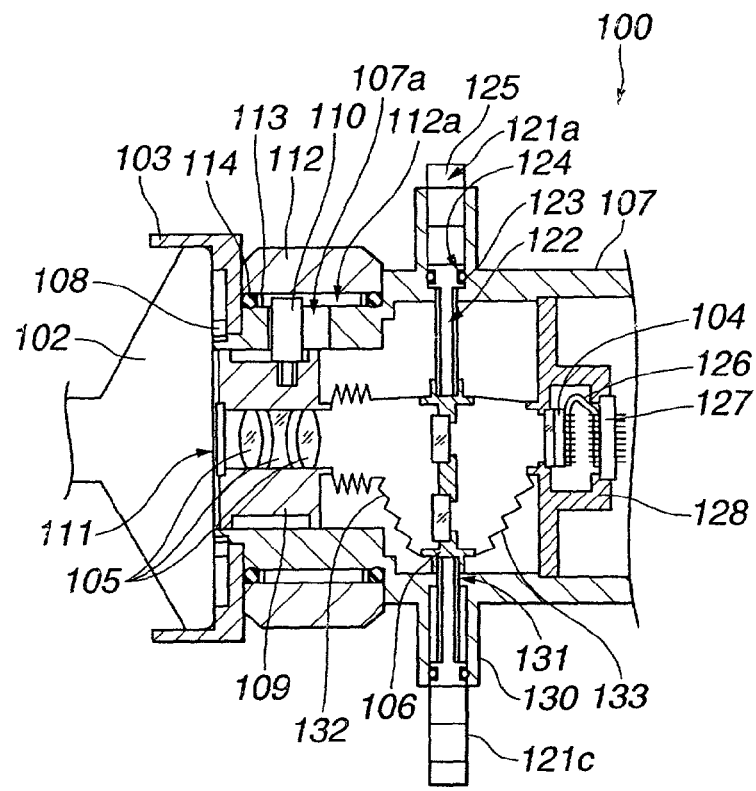
Figure 8:
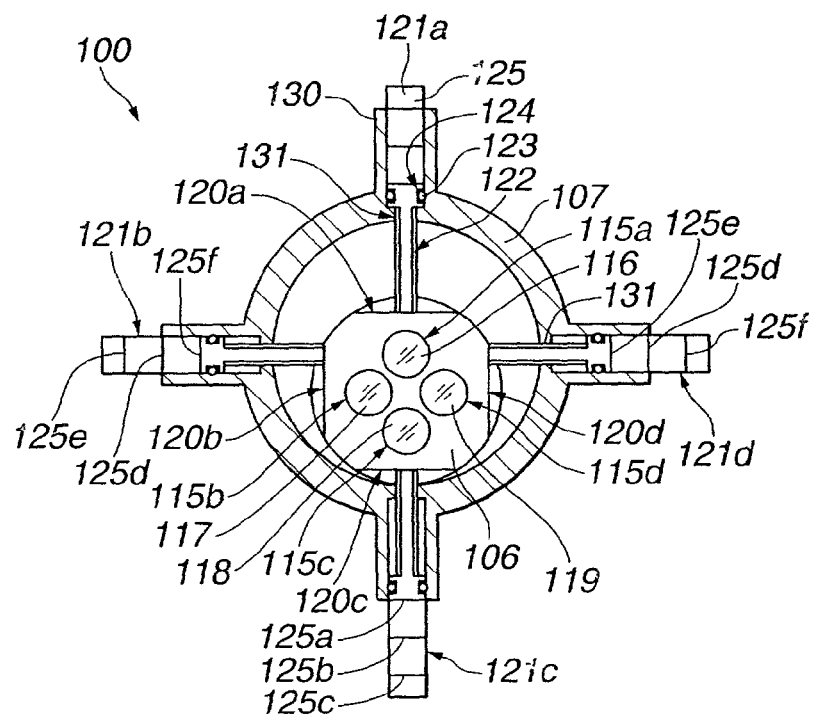

As shown in FIGS. 7 and 8, the endoscope imaging apparatus 100 of this embodiment is mainly composed of an endoscope mount 103, an imaging optical unit 111, a filter unit 106 to which optical members are disposed, a solid imaging element 104, for example, a CCD, or the like having an imaging surface on which an endoscope image is formed and converting the endoscope image into electric signals, and an imaging apparatus main body 107.

The endoscope mount 103 can detachably mounted on an endoscope 102 for observing, for example, the interior of a body cavity. The imaging optical unit 111 has at least one optical lens 105 disposed thereto to form an optical image from the endoscope 102 on the solid imaging element 104. The optical members of the filter unit 106 are disposed such that an endoscope image having passed through the imaging optical unit 111 transmits or passes therethrough. The imaging apparatus main body 107 contains the solid imaging element 104, an imaging optical unit 111, the filter unit 106, and the like.

The endoscope mount 103 is integrated with the imaging apparatus main body 107 by screwing a mount presser member 108 into the imaging apparatus main body 107. The optical lens 105 is airtightly joined in a lens frame 109 by, for example, soldering, or the like. At least a part of the outer peripheral surface of the lens frame 109 is engaged with the inner peripheral surface of the imaging apparatus main body 107, and a cam pin 110, which passes through a cam hole 107a defined through the imaging apparatus main body 107 obliquely with respect to an optical axis direction, is disposed to the lens frame 109.

The extreme end of the cam pin 110 projecting from the outside surface of the imaging apparatus main body 107 is inserted into and disposed in a linear cam groove 112a that is formed in parallel with an optical axis on the inner peripheral surface of a focus ring 112 disposed rotatably with respect to the imaging apparatus main body 107.

O-rings 114 are disposed to both the ends of the focus ring 112 through washers 113. With this arrangement, a watertight state is established between the imaging apparatus main body 107 and the focus ring 112.

Four openings 115a, 115b, 115c, and 115d, for example, are formed through the filter unit 106, and flat portions 120a, 120b, 120c, and 120d are formed around the outer peripheral surface of the filter unit 106 at four positions. Then, a fluorescent light observation filter 116 (optical lens) is disposed to, for example, the opening 115a, an infrared light observation filter 117 (optical lens) is disposed to the opening 115b, a zoom lens 118 (optical lens) for enlarging or reducing an endoscope image is disposed to the opening 115c, and the opening 115d is remained as an opening or a visible light observation filter 119 (optical lens) is disposed to the opening 115d, respectively.

The extreme end surfaces of adjustment pins 121a, 121b, 121c, and 121d for dislocating the filter unit 106 in a direction vertical to an optical axis are abutted against the flat portions 120a, 120b, 120c, and 120d, respectively.

These adjustment pins 121a, 121b, 121c, and 121d are composed of screw portions 122 screwed into the imaging apparatus main body 107, recessed portions 124 in which O-rings 123 are disposed to maintain water tightness, and knob portions 125 that are held when the screw portions 122 are screwed into the imaging apparatus main body 107. These adjustment pins 121a, 121b, 121c, and 121d are disposed so as to pass through the imaging apparatus main body 107. The disposition of the O-rings 123 in the recessed portions 124 keeps the portion between the imaging apparatus main body 107 and the adjustment pins 121 in a water-tight state.

The knob portions 125 of the adjustment pins 121a and 121c have marks for making it easy to dispose the openings 115a, 115b, 115c, and 115d in a light path. For example, the adjustment pin 121a has an indicator 125a formed around the entire periphery thereof to indicate that the opening 115a is located in the light path, an indicator 125b for indicating that the opening 115b or 115d is located in the light path, and an indicator 125c for indicating that the opening 115c is located therein, as shown in FIG. 9A.

Further, the knob portions 125 of the adjustment pins 121b and 121d have an indicator 125d for indicating that the opening 115a or 115c is located in the light path, an indicator 125e for indicating that the opening 115d is located in the light path, and an indicator 125f for indicating that the opening 115d is located in the light path.

Note that indicators having a desired recognizable shape, configuration, and size such as a round mark as shown in FIG. 9B, and the like may be used as the indicators 125a, . . . , 125f, in addition to the line around the entire periphery shown in 9A.

The solid imaging element 104 is connected to a hermetic connector 127 through a flexible substrate 126 on which an imaging element drive circuit is formed. These solid imaging element 104, flexible substrate 126, and hermetic connector 127 are contained in an imaging element frame 128. The hermetic connector 127 is airtightly joined to the imaging element frame 128.

The lens frame 109 is airtightly joined to the filter unit 106 and the filter unit 106 is airtightly joined to the imaging element frame 128 by tube members 132 and 133 each having a metal tubular elastic bellows portion formed thereto, respectively. That is, the space from the lens frame 109 to the imaging element frame 128 is maintained in an airtight state.

As shown in FIG. 10, the tube member 132 includes an optical axis expandable portion 132a that is expandable in the optical axis direction and a vertically expandable portion 132b that is expandable in a direction vertical to the optical axis direction. In contrast, the tube member 133 is formed so as to be expandable in a direction vertical to the optical axis.

Note that a crystal filter may be disposed in the opening 115 of the filter unit 106 to reduce moiré when a fiber scope is used, or four types of zoom lenses having a different magnification may be disposed therein.

Figure 12:
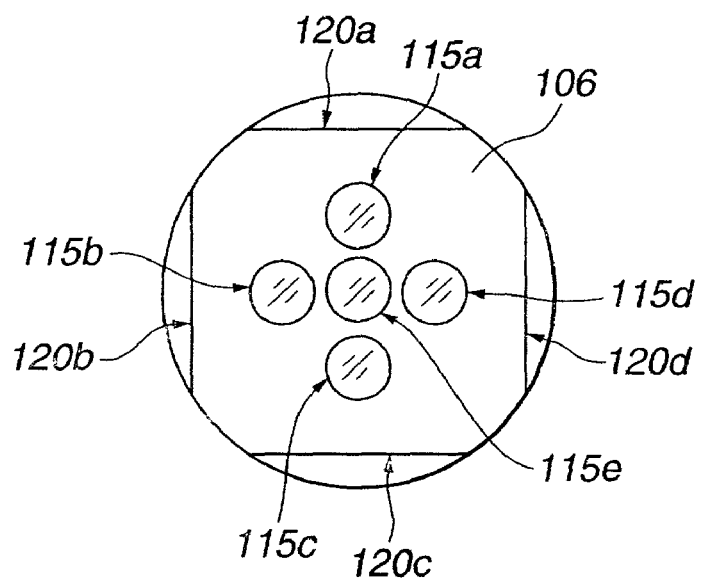

Further, the number of the openings 115 of the filter unit 106 is not limited to the four sets, and two openings 115a and 115b or five openings 115a, . . . , 115e may be used as shown in FIG. 11 or 12, or any other arrangements may be used.

Further, although not shown, the solid imaging element 104 is fixed to the imaging apparatus main body 107 in a state it is aligned with the optical axis of the imaging optical unit 111.

Further, four opening projections 130, in which the adjustment pins 121 are disposed, are formed to the imaging apparatus main body 107 at predetermined positions. Female screw portions 131, into each of which the thread portion 122 of each adjustment pin 121 is screwed, are formed around the inner peripheral surfaces the opening projections 130.

Operation of the endoscope imaging apparatus 100 arranged as described above will be described.

When observation is performed using ordinary illumination light, the imaging apparatus main body 107 is adjusted such that the filter 119 of the filter unit 106 is located in the light path by changing the positions where the respective adjustment pins 121a, 121b, 121c, and 121d are screwed.

Specifically, for example, the adjustment pins 121a and 121c are adjusted first such that the indicator 125b is disposed at a predetermined position with respect to the imaging apparatus main body 107, that is, the filter unit 106 is adjusted in an up and down direction with respect to the sheet surface.

Next, the adjustment pins 121b and 121d are adjusted to thereby adjust the filter unit 106 in a vertical direction with respect to the sheet surface so that the indicator 125f is disposed at a predetermined position with respect to the imaging apparatus main body 107. When these adjustment jobs are carried out, the tube members 132 and 133 expand and contract, respectively.

Next, the endoscope mount 103 is connected to the endoscope 102, and a focus is adjusted by rotating the focus ring 112. Specifically, the cam pin 110 fitted into the linear cam groove 112a is pressed by rotating the focus ring 112. Thus, the cam pin 110 moves along the cam hole 107a formed through the imaging apparatus main body 107. At this time, the lens frame 109 (imaging optical unit 111) integrated with the cam pin 110 is moved back and forth in the optical axis direction because the cam hole 107a is formed in an oblique direction with respect to the optical axis, thereby the focus can be adjusted. At this time, the bellows portion expands and contracts in the optical axis direction.

When an endoscope image is formed on the imaging surface of the solid imaging element 104 by performing the aforementioned operation, the endoscope image is converted into electric signals and can be observed on a monitor.

Next, a case in which the observation using the ordinary light is changed to observation using fluorescent light.

To perform the fluorescent light observation, the fluorescent light observation filter 116 is disposed in the light path. For this purpose, first, the adjustment pins 121a and 121c are adjusted to thereby adjust the filter unit 106 in the up and down direction on the sheet surface so that the indicator 125a is located at a predetermined position of the imaging apparatus main body 107.

Next, the adjustment pins 121b and 121d are adjusted. Then, the filter unit 106 is adjusted in the vertical direction with respect to the sheet surface so that the indicator 125d is located at a predetermined position of the imaging apparatus main body 107. At this time, a focus is adjusted when necessary by rotating the focus ring 112. The endoscope imaging apparatus 100 is changed from the ordinary observation state to the fluorescent light observation state by performing these operations.

Note that an observation state can be changed to an infrared light observation state and to an enlarged observation state by disposing the infrared light observation filter 117 and the zoom lens 118 in the light path, respectively by performing similar operations.

Then, after the endoscope imaging apparatus 100 is used, it can be subjected to autoclave sterilization as it is because the components thereof from the optical lens 105 to the solid imaging element 104 are disposed in the same airtight unit.

As described above, the endoscope imaging apparatus is arranged such that the filter unit, in which the plurality of filters (optical lenses) are disposed in correspondence to the types of illumination lights emitted from a light source unit, is interposed between the imaging optical unit and the imaging element frame; the imaging optical unit is airtightly joined to the filter unit and the imaging element frame is airtightly joined to the filter unit through the metal tube members to which the bellows portions are formed, respectively; and the adjustment members are disposed in the imaging apparatus main body to adjust the positions of the filters disposed in the filter unit with respect to the optical axis. Accordingly, the endoscope imaging apparatus, in which the filters can be changed easily and which has excellent operability and can be subjected to autoclave sterilization, can be provided in a less expensive structure.

Figure 13:
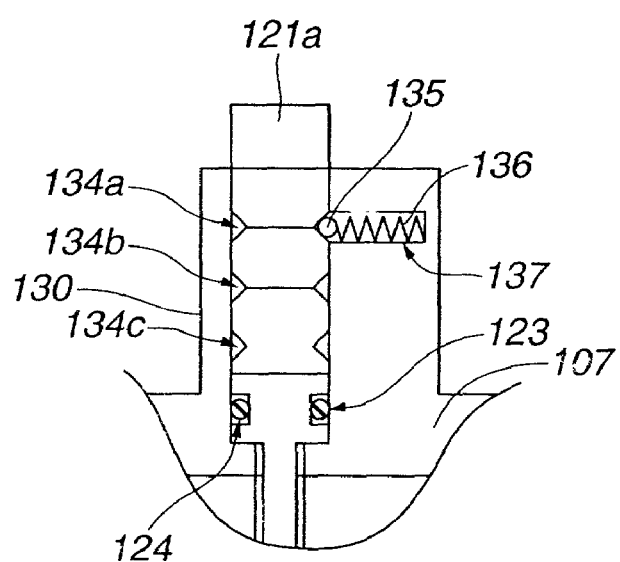
FIG. 13 is a view explaining another arrangement of a filter change mechanism.

Note that three V-shaped grooves 134, for example, may be formed to each adjustment pin 121 in place of the screw portion 122, as shown in FIG. 13.

That is, each of the adjustment pins 121a and 121c is provided with a V-shaped groove 134a into which a lock ball 135, which will be described later, is fitted when the opening 115a is disposed in the light path, a V-shaped groove 134b into which the lock ball 135 is fitted when the opening 115b or 115d is disposed in the light path, and a V-shaped groove 134c into which the lock ball 135 is fitted when the opening 115d is disposed in the light path.

Further, each of the adjustment pins 121b and 121d is provided with a V-shaped groove 134d (not shown) into which a lock ball 135 is fitted when the opening 115a or 115c is disposed in the light path, a V-shaped groove 134 (not shown) into which the lock ball 135 is fitted when the opening 115b is disposed in the light path, and a V-shaped groove 134f (not shown) into which the lock ball 135 is fitted when the opening 115d is disposed in the light path.

In contrast, the imaging apparatus main body 107 is provided with recessed portions 137, in which elastic members 136, for example, coil springs are disposed, in place of the female screw portions 131. Then, the elastic member 136 having the lock ball 135 at an end thereof is disposed each recessed portion 137. The length of the elastic members 136 is set to a length for permitting the lock balls 135 to press the adjustment pins 121 with an appropriate amount of force.

Operation of the endoscope imaging apparatus arranged as described above will be described.

In the ordinary light observation, the respective adjustment pins 121 are pressed and adjusted such that the filter 119 of the filter unit 106 is located in the light path. Specifically, first, the adjustment pin 121a or 121c is pressed to thereby adjust the filter unit 106 in the up and down direction on the sheet surface so that the indicator 125b is located at the predetermined position with respect to the imaging apparatus main body 107. At the time, the lock balls 135 are fitted into the V-shaped grooves 134b of the adjustment pins 121a and 121c by the elastic force of the elastic members 136, thereby a feeling of click is produced, and, at the same time, the adjustment pins 121a and 121c are fixedly held.

Next, the adjustment pin 121b or 121d is pressed to thereby adjust the filter unit 106 in the vertical direction on the sheet surface so that the indicator 125f is located at the predetermined position with respect to the imaging apparatus main body 107. At the time, the lock balls 135 are fitted into the V-shaped grooves 134f of the adjustment pins 121b and 121d by the elastic force of the elastic members 136, thereby a feeling of click is produced, and, at the same time, the adjustment pins 121b and 121d are fixedly held.

That is, when a filter is changed, the V-shaped groove into which the lock ball 135 is fitted is changed by moving the positions of the respective adjustment pins 121. With this operation, a filter can be smoothly changed, similarly to the above arrangement.

Figure 14:
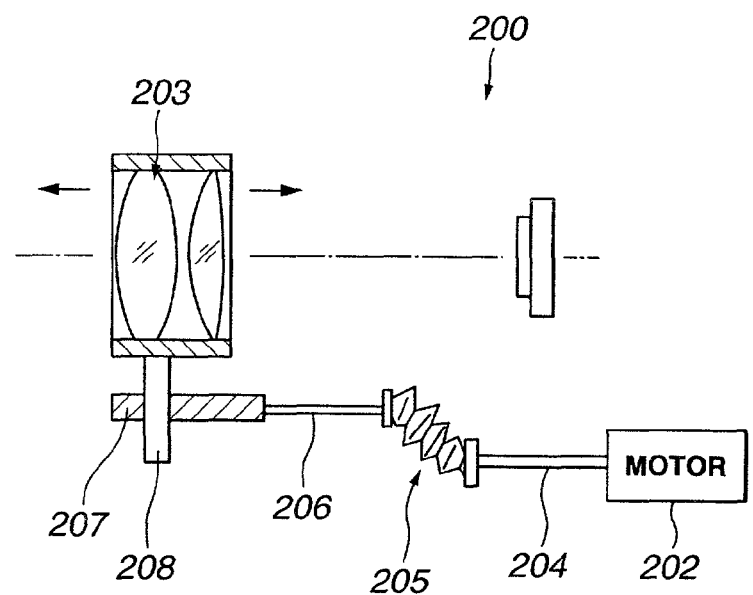
FIG. 14 is a view explaining an arrangement of a power transmission unit of an endoscope imaging apparatus according to a fifth embodiment.

A fifth embodiment of the present invention will be described below with reference to FIG. 14.

As shown in the figure, in an endoscope imaging apparatus 200 of this embodiment, a motor shaft 204 is fixedly coupled with an adjustment shaft 206 for performing a focus adjustment and zooming through a bellows 205 acting as a metal tubular elastic member.

The motor shaft 204 extends from, for example, a motor 202 rotated by electric power as a rotary power source in an optical axis direction. The adjustment shaft 206 performs the focus adjustment and zooming by being moved and extends in the optical axis direction. A lead screw 207 is fixed to the other end of the adjustment shaft 206 and screwed into a support projection 208 projecting from a lens unit 203.

With this arrangement, the lead screw 207 is rotated by the rotational drive force of the motor 202 through the motor shaft 204, the bellows 205, and the adjustment shaft 206, thereby the lens unit 203 integrated with the support projection 208 is moved back and forth. With this operation, the focus adjustment and the zooming can be carried out.

Operation of the endoscope imaging apparatus 200 arranged as described above will be described.

When the motor 202 rotates, the motor shaft 204 coupled with the motor 202 is rotated. Then, this rotation is transmitted to the adjustment shaft 206 coupled with and fixed to the other end of the bellows 205 through the bellows 205 coupled with and fixed to the motor shaft 204, thereby the adjustment shaft 206 is rotated.

Thus, the lead screw 207 connected to the end of the adjustment shaft 206 is rotated to thereby move the lens unit 203 integrated with the support projection 208 in the optical axis direction shown by arrows in the figure. With this operation, the focus or zooming adjustment can be carried out.

The shaft disposed to the motor is coupled with the shaft disposed to the lens unit through the bellows acting as the tubular elastic member, thereby the bellows absorbs the misalignment between the shafts so that the rotation of the motor shaft can be smoothly transmitted to the shaft and the position of the lens unit can be adjusted in the optical axis direction.

This arrangement makes it unnecessary to strictly dispose the motor shaft 204 and the adjustment shaft 206 on the same axis, which can save an excessively high cost resulting from requirements for overaccurately processing parts. Accordingly, cost can be reduced.

Further, even if a power transmission system cannot be disposed linearly due to the disposition of parts and mechanisms other than the power transmission system, the provision of the bellows can greatly improve the degree of freedom of design by optionally setting the misalignment and angle of axes.

Figure 15A:
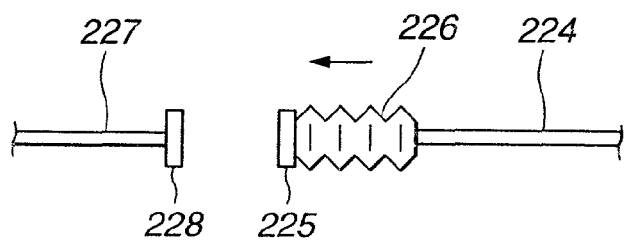
FIG. 15A is a view explaining an arrangement of a power transmission unit of an endoscope imaging apparatus.
Figure 15B:
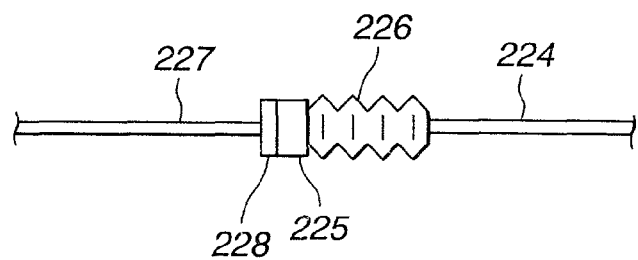
FIG. 15B explains a power transmitting state of the power transmission unit.

Note that a bellows 226 having a flat plate 225 disposed thereto is attached to an end of one shaft 224, and a flat plate 228 facing the flat plate 225 is attached to an end of the other shaft 227, as shown in FIG. 15A, in place of that the shafts are directly coupled with and fixed to each other through the bellows as described above. Then, as shown in FIG. 15B, the two flat plates 225 and 228 are pressed against and fixed to each other by the press force, that is, the elastic force of the bellows 226.

With this arrangement, the flat plates 225 and 228 are pressed against each other by the elastic force of the bellows 226, thereby rotation is transmitted by the frictional force acting between the flat plates 225 and 228.

Further, since the flat plates 225 and 228 can slide on each other, when a force greater than a predetermined amount is applied to the flat plates 225 and 228, they are released from a pressed and intimate contact state, thereby a large amount of rotational force can be discharged.

With this operation, workability in assembly can be eased because the assembly of the power transmission system is completed by pressing the flat plate disposed to the shaft against the flat plate disposed to the bellows by the elastic force of the bellows, in addition to the above effect.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope imaging apparatus, comprising:
   an optical system including at least one optical lens for obtaining an optical image of a subject;
   an optical system support member for supporting the optical system;
   an imaging element for capturing an optical image from the optical system;
   an imaging element support member for supporting the imaging element;
   a tubular member comprising a first end and a second end that oppose each other, the tubular member defining an inner space extending therethrough and between the first end and the second end, the optical system support member being hermetically joined to the first end and the imaging element support member being hermetically joined to the second end in order to—airtightly seal the inner space, the tubular member further comprising an airtightness-maintaining and position-adjusting portion between said first and second ends adapted to maintain the airtight seal of the inner space in response to relative movements of the optical system support member and the imaging element support member and adapted to allow adjustment of relative positions of the optical system support member and the imaging element support member, the airtightness-maintaining and position-adjusting portion expanding and contracting for distance adjustment and deforming for position adjustment such that an optical axis of said at least one optical lens of the optical system support member and an optical axis of an imaging surface of said imaging element of the imaging element support member coincide with each other in the tubular member;
   an adjustment mechanism for adjusting relative positions of the optical system support member and the imaging element support member in three dimensions, said three dimensions being a direction of the optical axis optical system, a direction orthogonal to the direction of the optical axis and a tilt direction to the optical axis and for maintaining a state of adjustment after performing the adjustment; and
   an adjustment frame having the adjustment mechanism dispose through the adjustment frame, the adjustment frame connecting the optical system support member and the imaging element support member so as to form a space where a deformed part of the airtightness-maintaining and position-adjusting portion in the direction orthogonal to the direction of the optical axis which is caused by movements of the optical system support member and the imaging element support member is located.

2. An endoscope imaging apparatus according to claim 1, wherein the optical system support member further comprises an optical system fixing portion for fixing the optical system and an optical system frame member defining an inner space in which the optical system fixing portion is located, the optical system frame member being hermetically joined to the tubular member.

3. An endoscope imaging apparatus according to claim 1, wherein the imaging element support member further comprises an imaging element fixing portion for fixing the imaging element and an imaging element frame member defining an inner space in which the imaging element fixing portion is located, the imaging element frame member being hermetically joined to the tubular member.

4. An endoscope imaging apparatus according to claim 1, wherein the adjusting mechanism moves the optical system support member relative to the imaging element support member.

5. An endo scope imaging apparatus according to claim 1, wherein the adjusting mechanism moves the imaging element support member relative to the optical system support member.

6. An endoscope imaging apparatus according to claim 1, wherein the adjusting frame moves the optical system support member and the imaging element support member relative to each other.

7. An endoscope imaging apparatus according to claim 6, wherein the adjusting frame moves the optical system support member relative to the imaging element support member.

8. An endoscope imaging apparatus according to claim 6, wherein the adjusting frame moves the imaging element support member relative to the optical system support member.

9. An endoscope imaging apparatus according to claim 6, wherein the optical system support member comprises an optical system fixing portion for fixing the optical system and an optical system frame member defining an inner space in which the optical system fixing portion is located, the adjusting frame moving the optical system frame member relative to the imaging element support member.

10. An endoscope imaging apparatus according to claim 9, wherein the adjustment mechanism includes a plurality of screws disposed through the adjustment frame.

11. An endoscope imaging apparatus according to claim 10, wherein the plurality of screws are disposed through the adjustment frame and abut against an external surface of the optical system frame member.

12. An endoscope imaging apparatus according to claim 11, wherein each of the plurality of screws is adapted to rotate to move the optical system frame member in an axial direction, orthogonal direction to an optical axis and a tilt direction.

13. An endoscope imaging apparatus according to claim 10, wherein the plurality of screws are disposed through the adjustment frame and abut against an external surface of an image element frame member.

14. An endoscope imaging apparatus according to claim 13, wherein each of the plurality of screws is adapted to rotate to move the image element frame member in an axial direction, orthogonal direction to an optical axis and a tilt direction.

15. An endoscope imaging apparatus according to claim 6, wherein the imaging element support member comprises an imaging element fixing portion for fixing the imaging element and an imaging element frame member defining an inner space in which the imaging element fixing portion is located, and wherein the adjusting frame moves the imaging element frame member relative to the optical system support member.

16. An endoscope imaging apparatus according to claim 1, further comprising a filter unit located in the inner space of the tubular member and between the optical system and the imaging element for selecting one of a plurality of observation states.

17. An endoscope imaging apparatus according to claim 16, wherein the plurality of observation states comprise a normal light observation state, an enlarged observation state, and a fluorescent light observation state.

18. An endoscope imaging apparatus according to claim 17, wherein the filter unit defines an opening for the normal light observation state.

19. An endoscope imaging apparatus according to claim 16, wherein the filter unit defines an opening.

20. An endoscope imaging apparatus according to claim 16, wherein the filter unit defines a plurality of openings, each of the plurality of openings comprising one of a filter and a lens.

21. An endoscope imaging apparatus according to claim 16, wherein the filter unit is hermetically joined to the tubular member thereby airtightly sealing the inner space of the tubular member.

22. An endoscope imaging apparatus according to claim 21, wherein the filter unit defines a plurality of openings and comprises a plurality of filters, at least one of the plurality of openings or one the plurality of filters being selected according to the observation state, and the endoscope imaging apparatus further comprises a filter unit moving mechanism to move the filter unit in a direction perpendicular to the direction of the optical axis of the optical system to change the observation state while maintaining the hermetic seal of the inner space of the tubular member and position one of the plurality of filters or one of the plurality of openings on the optical axis according to the observation state.

23. An endoscope imaging apparatus according to claim 1, wherein the adjustment mechanism is located outside of an airtightly sealed area formed from the tubular member, optical system support member and image element support member.

24. An endoscope imaging apparatus according to claim 1, wherein the imaging element support member and the optical system support member are separated by the airtightness-maintaining and position-adjusting portion.

25. An endoscope imaging apparatus according to claim 1, wherein the airtightness-maintaining and position-adjusting is a bellows portion formed into a tubular body.

26. An endoscope imaging apparatus according to claim 25, wherein the bellows portion is airtightly sealed.

* * * * *